(12) United States Patent
Kitamoto (10) Patent No.: US 9,101,934 B2
(45) Date of Patent: Aug. 11, 2015

(54) LIQUID HANDLING APPARATUS

(71) Applicant: Enplas Corporation, Saitama (JP)

(72) Inventor: Ken Kitamoto, Saitama (JP)

(73) Assignee: ENPLAS Corporation, Saitama (JP)

( * ) Notice: Subject to any disclaimer, the term of this patent is extended or adjusted under 35 U.S.C. 154(b) by 0 days.

(21) Appl. No.: 14/057,873

(22) Filed: Oct. 18, 2013

(65) Prior Publication Data

US 2014/0112838 A1 Apr. 24, 2014

(30) Foreign Application Priority Data

Oct. 18, 2012 (JP) ................. 2012-230743
Aug. 26, 2013 (JP) ................. 2013-174420

(51) Int. Cl.
| | |
|---|---|
| *B01L 3/00* | (2006.01) |
| *B81B 1/00* | (2006.01) |
| *B81B 7/00* | (2006.01) |
| *G01N 35/00* | (2006.01) |

(52) U.S. Cl.
CPC ....... *B01L 3/502746* (2013.01); *B01L 3/50273* (2013.01); *B01L 2200/027* (2013.01); *B01L 2200/0684* (2013.01); *B01L 2300/087* (2013.01); *B01L 2300/0816* (2013.01); *B01L 2300/0838* (2013.01); *B01L 2300/0867* (2013.01); *B01L 2400/0406* (2013.01); *B01L 2400/0487* (2013.01); *B01L 2400/086* (2013.01); *G01N 2035/00158* (2013.01)

(58) Field of Classification Search
None
See application file for complete search history.

(56) References Cited

U.S. PATENT DOCUMENTS

| | | | |
|---|---|---|---|
| 2002/0079219 A1* | 6/2002 | Zhao et al. .................... 204/451 |
| 2009/0045058 A1* | 2/2009 | Fujita et al. ................... 204/451 |
| 2009/0074623 A1* | 3/2009 | Park et al. ..................... 422/100 |
| 2009/0107909 A1* | 4/2009 | Kotera et al. ................. 210/513 |
| 2010/0261205 A1* | 10/2010 | Kakuta et al. ................ 435/7.92 |
| 2010/0267066 A1* | 10/2010 | Hosokawa et al. ............. 435/13 |
| 2011/0028353 A1 | 2/2011 | Aoyagi et al. |
| 2011/0036152 A1* | 2/2011 | Park et al. ..................... 73/64.56 |
| 2011/0065591 A1* | 3/2011 | Takagi ............................. 506/7 |
| 2014/0079602 A1* | 3/2014 | Ono .............................. 422/502 |

FOREIGN PATENT DOCUMENTS

JP 2008-180699 A 8/2008

* cited by examiner

*Primary Examiner* — Jennifer Wecker
(74) *Attorney, Agent, or Firm* — Brundidge & Stanger, P.C.

(57) ABSTRACT

A liquid handling apparatus includes a substrate that includes a groove which is a channel through which a liquid can be moved on the basis of a capillary phenomenon, and a film that is bonded to the substrate to cover the opening of the groove, in which the channel has a main channel and a guide channel, the groove has a main groove that is the main channel by the film being bonded to the substrate, and a guide groove that is the guide channel by the film being bonded to the substrate, opens on a lateral surface of the main groove, and has a width narrower than the width of the main groove, and the guide groove is placed in an area on a film side of the lateral surface of the main groove and shallower than the main groove.

7 Claims, 10 Drawing Sheets

LIQUID HANDLING APPARATUS

CROSS REFERENCE TO RELATED APPLICATIONS

This application is entitled and claims the benefit of Japanese Patent Application No. 2012-230743, filed on Oct. 18, 2012, and Japanese Patent Application No. 2013-174420, filed on Aug. 26, 2013, the disclosure of which including the specification, drawings and abstract is incorporated herein by reference in its entirety.

TECHNICAL FIELD

The present invention relates to a liquid handling apparatus that is used in liquid sample analysis, processing, and the like.

BACKGROUND ART

In recent years, microchannel chips have been in use for the high-precision and high-speed analysis of trace substances such as proteins and nucleic acids. The microchannel chips have advantages in that even a small amount of reagent or sample suffices, and thus use in various applications such as clinical inspection, food inspection, and environmental inspection are expected.

The microchannel chip has a channel, a chamber, and the like, and a liquid can be moved in the channel on the basis of a capillary phenomenon. In a case where the width of the channel of the microchannel chip is sufficiently narrow, the speed of movement of the liquid is almost the same in a central part and both end parts in the width direction of the channel. In a case where the width of the channel is wide to some extent, the speed of movement of the liquid differs substantially at the central part and both of the end parts in the width direction of the channel. Therefore, in a case where the width of the channel is wide to some extent, the speed of movement of the liquid is not uniform so bubbles remain in the channel.

In order to solve the problem, a microchannel chip whose depth is different in a central portion and both end parts in the width direction of a channel has been proposed (for example, refer to PTL 1). The microchannel chip described in PTL 1 has a pair of grooves formed in the depth direction at both of the width-direction end parts of a bottom surface of the channel which is formed on a substrate formed of resin. The pair of grooves reduce the resistance with respect to a liquid moving through both of the width-direction end parts of the channel and increase the speed of movement of the liquid moving through both of the width-direction end parts of the channel. In the microchannel chip described in PTL 1, the speed of movement of the liquid can be uniform to some extent at the central portion and both of the end parts in the width direction of the channel, and thus bubbles can be prevented from remaining in the channel.

CITATION LIST

Patent Literature

PTL 1
Japanese Patent Application Laid-Open No. 2008-180699

SUMMARY OF INVENTION

Technical Problem

However, when the substrate of the microchannel chip described in PTL 1 is produced, deep grooves have to be formed at both of the width-direction end parts. Therefore, it is difficult to manufacture a mold for a highly uneven molded article and the deep groove portion has low moldability.

An object of the present invention is to provide a liquid handling apparatus in which bubbles are unlikely to remain in a channel even after the introduction of a liquid and which can be manufactured with ease.

Solution to Problem

In order to achieve the above objective, a liquid handling apparatus of the present invention includes a substrate that includes a groove which is a channel through which a liquid can be moved on the basis of a capillary phenomenon by an opening of the groove being closed, and a film that is bonded to the substrate to cover the opening of the groove, in which the channel has a main channel and a guide channel, the groove has a main groove that is the main channel by the film being bonded to the substrate, and a guide groove that is the guide channel by the film being bonded to the substrate, opens on a lateral surface of the main groove, and has a width narrower than the width of the main groove, and the guide groove is placed in an area on a film side of the lateral surface of the main groove and shallower than the main groove.

Advantageous Effects of Invention

According to the present invention, a liquid handling apparatus that has a channel in which bubbles are unlikely to remain even after introduction of a liquid, has high moldability, and facilitates manufacturing of a mold can be provided.

DESCRIPTION OF EMBODIMENTS

Hereinafter, embodiments according to the present invention will be described in detail referring to the accompanying drawings. In the following description, a microchannel chip will be described as a representative example of a liquid handling apparatus according to the present invention. In the present specification, 'film' means a thin and flat plate-shaped member. Examples of the 'film' include thin plates as well as thin films.

[Configuration of Microchannel Chip]

Figure 1A:
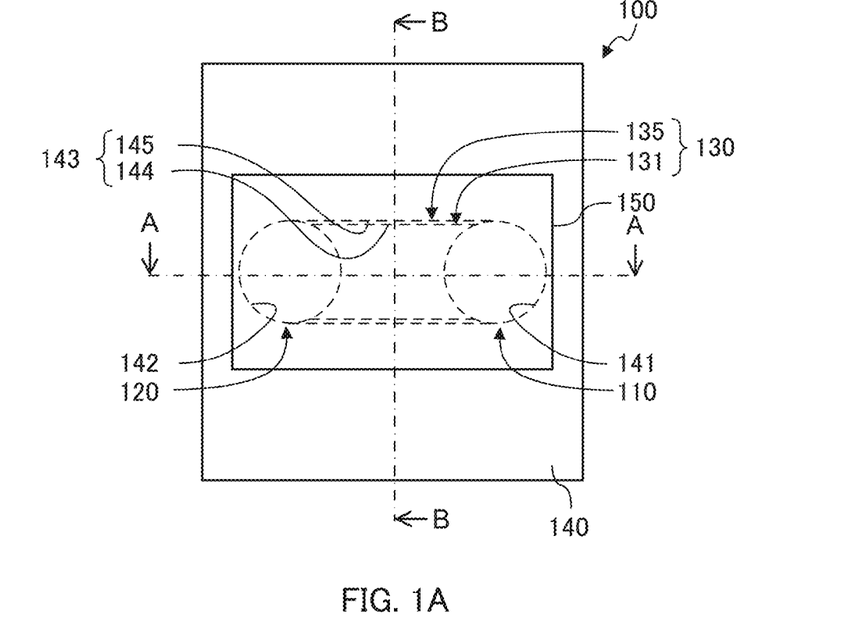
FIGS. 1A to 1C are views showing the configuration of a microchannel chip according to Embodiment 1.
Figure 1B:
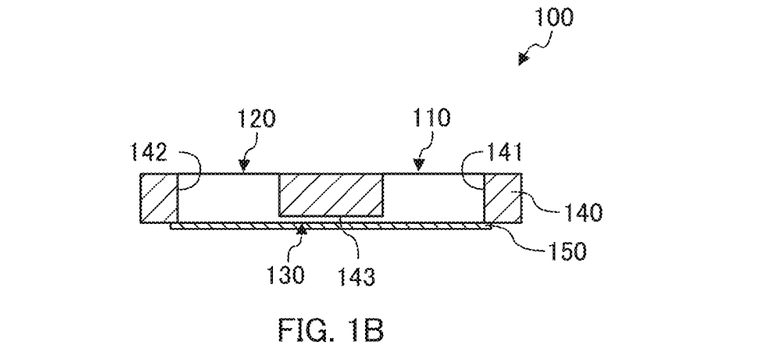
Figure 1C:
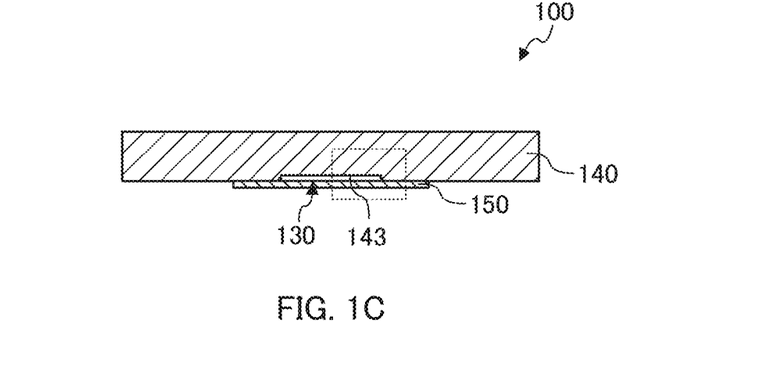
Figure 2:
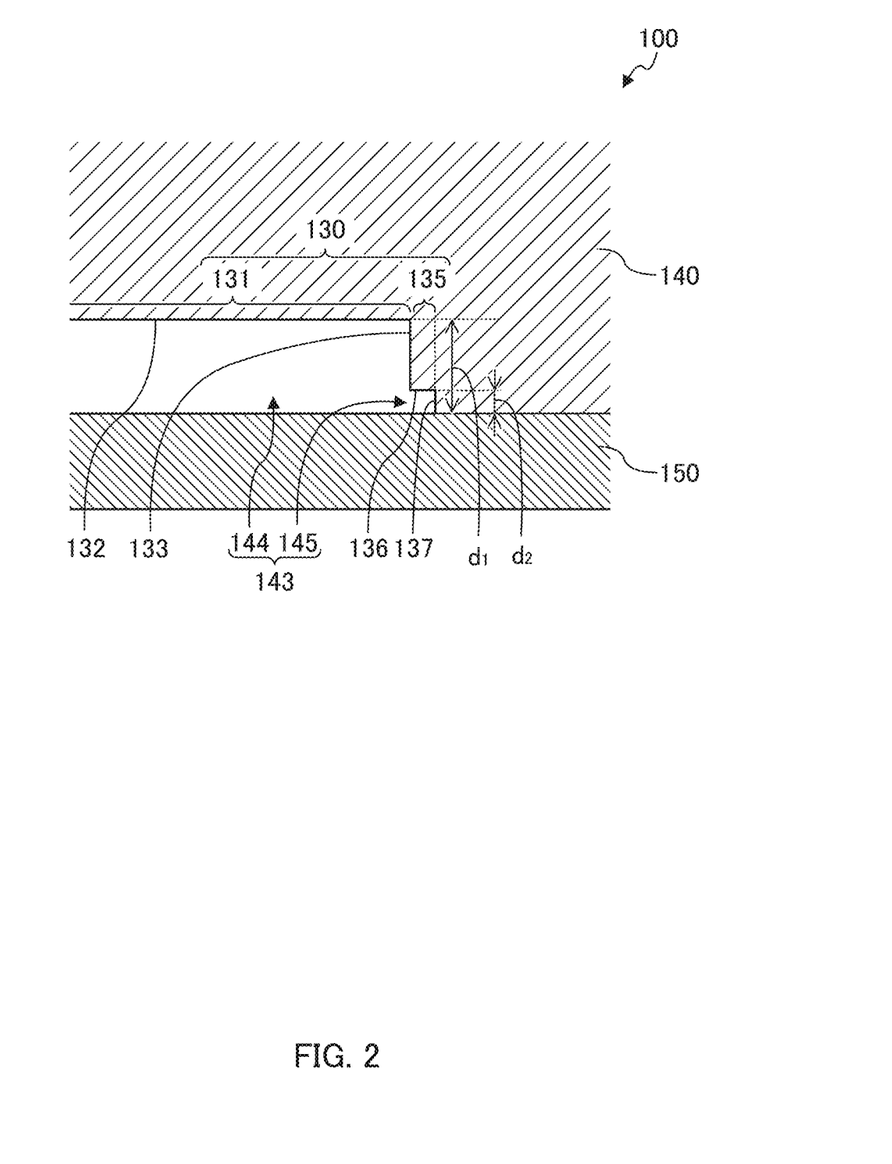
FIG. 2 is a partially enlarged cross-sectional view of FIG. 1C.
Figure 3A:
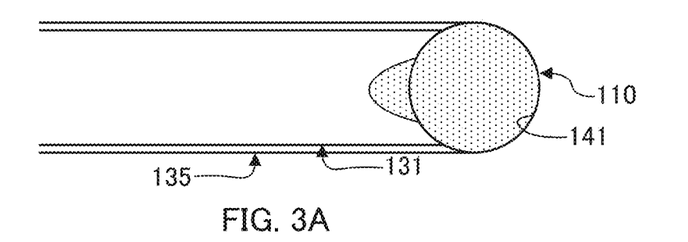
FIGS. 3A to 3E are schematic views showing the movement of a liquid in a channel of the microchannel chip according to Embodiment 1.
Figure 3B:
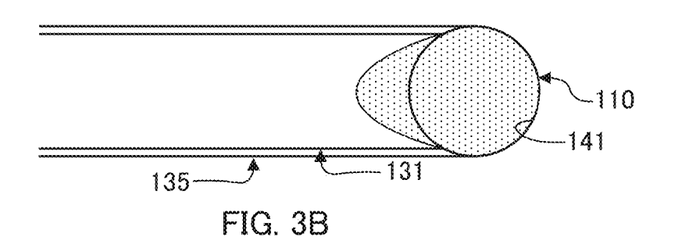
Figure 3C:
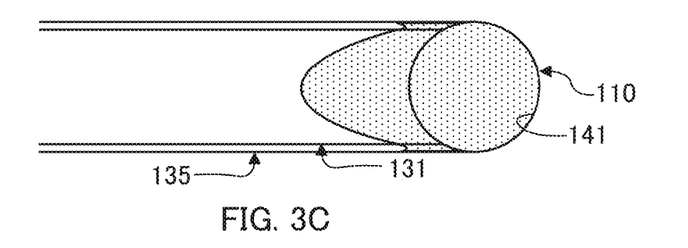
Figure 3D:
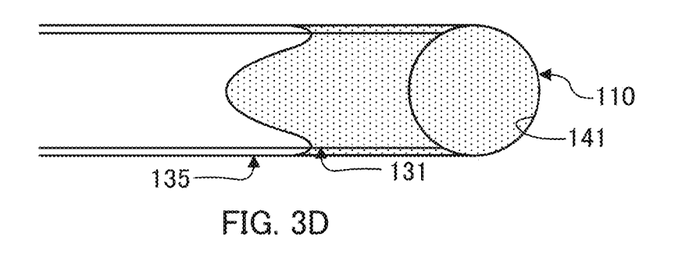
Figure 3E:
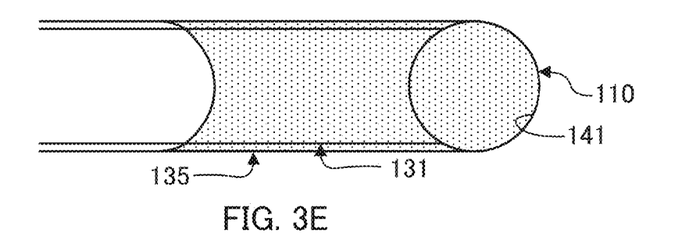

FIGS. 1A to 1C are views showing the configuration of microchannel chip 100 according to Embodiment 1 of the present invention. FIG. 1A is a bottom view of microchannel chip 100, FIG. 1B is a cross-sectional view taken along line A-A shown in FIG. 1A, and FIG. 1C is a cross-sectional view taken along line B-B shown in FIG. 1A. FIG. 2 is a partially enlarged cross-sectional view showing the area surrounded by the broken line in FIG. 1C.

As shown in FIGS. 1A to 1C, microchannel chip 100 is a plate-shaped device that includes two bottomed concave parts (first concave part 110 and second concave part 120) and channel 130. First concave part 110 and second concave part 120 communicate with each other via channel 130. First concave part 110 functions as an introduction inlet that introduces a liquid into channel 130. Second concave part 120 functions as an outlet through which the liquid in channel 130 is taken out.

As shown in FIGS. 1A to 1C, microchannel chip 100 includes substrate 140 and film 150.

Substrate 140 is a transparent and approximately rectangular member. Substrate 140 has first through hole 141, second through hole 142, and groove 143. First through hole 141 and second through hole 142 are formed to penetrate substrate 140. Since an opening on an opening side of groove 143 is closed by film 150, each of first through hole 141 and second through hole 142 is the bottomed concave part (first concave part 110 and second concave part 120). Since the opening is closed by film 150, groove 143 is channel 130 (refer to FIGS. 1B and 1C for both).

First through hole 141 communicates with one end part of groove 143. Second through hole 142 communicates with the other end part of groove 143. The shape of first through hole 141 and second through hole 142 is not particularly limited, and examples thereof include an approximately columnar shape. The diameter of first through hole 141 and second through hole 142 is not particularly limited, and examples thereof include approximately 6 mm.

Groove 143 has first groove 144 (a main groove) and second groove 145 (a guide groove) that is open on a lateral surface of first groove 144. Microchannel chip 100 according to the present invention is mainly characterized by the shape of groove 143 (channel 130), which will be described in detail later.

The type of a material constituting substrate 140 is not particularly limited but may be appropriately selected from known resins and glass. Examples of resins constituting substrate 140 include polyethylene terephthalate, polycarbonate, polymethyl methacrylate, vinyl chloride, polypropylene, polyether, and polyethylene. The thickness and color of substrate 140 are not particularly limited. For example, the thickness of substrate 140 is between 1 and 10 mm.

Film 150 is a transparent and approximately rectangular resin film bonded to one of surfaces of substrate 140 (refer to FIG. 1A). For example, film 150 and substrate 140 are bonded by thermocompression. Film 150 covers the opening of groove 143, an opening of first through hole 141 on the opening side of groove 143, and an opening of second through hole 142 on the opening side of groove 143.

The thickness of film 150 is not particularly limited if the shape of first concave part 110, second concave part 120, and channel 130 can be maintained. For example, the thickness of film 150 is approximately 100 μm.

The type of a resin constituting film 150 is not particularly limited but may be appropriately selected from known resins. Examples of resins constituting film 150 are the same as the examples of the resins constituting substrate 140. From the viewpoint of improving adhesion between substrate 140 and film 150, it is preferable that the resins constituting film 150 be the same as the resins constituting substrate 140.

As described above, groove 143 has first groove 144 (the main groove) and second groove 145 (the guide groove) that is open on the lateral surface of first groove 144. Since the opening is closed by film 150, first groove 144 and second groove 145 are first channel 131 (a main channel) and second channel 135 (a guide channel), respectively. Both of first channel 131 and second channel 135 are channels through which a liquid can be moved on the basis of a capillary phenomenon. Inner surfaces of both of first channel 131 and second channel 135 are lyophilic.

First channel 131 is the main channel that allows the movement of most liquids. One end part of first channel 131 communicates with first concave part 110, and the other end part communicates with second concave part 120. The cross-sectional area and cross-sectional shape of first channel 131 are not particularly limited if a liquid can be moved therein on the basis of a capillary phenomenon. For example, the cross-sectional shape of first channel 131 in a direction orthogonal to the direction of movement of the liquid is approximately rectangular with a width of several millimeters and a depth of hundreds of micrometers. First channel 131 is configured to have first bottom surface 132, a pair of first lateral surfaces 133 that are placed at both width-direction end parts of first bottom surface 132, and an inner surface of film 150 that opposes first bottom surface 132. In the present specification, 'a cross-section of the channel in the direction orthogonal to the direction of movement of the liquid' is simply referred to as 'a channel cross section.'

Second channel 135 is the guide channel (a subchannel) that moves some of the liquid before the liquid is moved by the main channel. The liquid moving through second channel 135 moves faster than the liquid moving through first channel 131, and guides the direction of movement of the liquid moving through first channel 131. One end part of second channel 135 communicates with first concave part 110, and the other end part communicates with second concave part 120. Second channel 135 is placed in an area on a film 150 side of first lateral surface 133 of first channel 131. In other words, second channel 135 is placed at a depth-direction lower end part of first lateral surface 133. The cross-sectional shape of second channel 135 is not particularly limited. In an example shown in FIG. 2, the cross-sectional shape of second channel 135 is rectangular. Second channel 135 is configured to have second bottom surface 136, second lateral surface 137 that is placed at one width-direction end part of second bottom surface 136, and an inner surface of film 150 that opposes second bottom surface 136. Second channel 135 is formed in a groove shape that has an opening in first channel 131 (first lateral surface 133).

The depth and width of second channel 135 are not particularly limited if the above-described function can be achieved. Second channel 135 is shallower than first groove 144, and it is preferable that the ratio $(d_2/d_1)$ of the depth of second channel 135 $d_2$ to the depth of first channel 131 $d_1$ be equal to or less than 0.7. In a case where $d_2/d_1$ exceeds 0.7, the movement of the liquid moving through second channel 135 is not sufficiently faster than the movement of the liquid moving through first channel 131, and there is a concern that the function of second channel 135 could not be sufficiently achieved. It is preferable that the depth of second channel 135 be a depth at which second channel 135 is not blocked by film 150 melted during the bonding by thermocompression, specifically, at least 20 μm. The width of second channel 135 (second groove 145) is narrower than the width of first channel 131 (first groove 144). For example, in a case where the depth of first channel 131 is 100 μm and the width thereof is 6 mm, the depth of second channel 135 is approximately 20 μm and the width thereof is approximately 50 μm.

FIGS. 3A to 3E are schematic views (partially enlarged plan views) showing the movement of the liquid in the channel of microchannel chip 100 according to Embodiment 1. As shown in FIG. 3, when the liquid is introduced from first concave part 110 and the liquid reaches a central part of first channel 131, the movement of the liquid is started in the central portion of first channel 131 on the basis of a capillary phenomenon (refer to FIG. 3A). When the movement of the liquid in the central part of first channel 131 proceeds, the liquid reaches second channel 135 (refer to FIG. 3B). Immediately after then, the movement of the liquid is started on the basis of a capillary phenomenon in second channel 135 (refer to FIG. 3C). Since the movement of the liquid moving through second channel 135 is sufficiently faster than the movement of the liquid moving through first channel 131, a head part of the liquid moving through second channel 135 overtakes a head part of the liquid moving through first channel 131 (refer to FIGS. 3D and 3E). The liquid moving through first channel 131 is moved to be pulled by the liquid moving through second channel 135 which is disposed at both width-direction ends. In this manner, in a central part and both end parts in the width direction of channel 130, the liquid is moved almost uniformly, and thus bubbles are unlikely to remain in channel 130 in microchannel chip 100.

Modification Example

As described above, the cross-sectional shape of second channel 135 is not particularly limited in the microchannel chip according to Embodiment 1. A microchannel chip that has a different cross-sectional (channel cross section) shape in the second channel will be described as a modification example of the microchannel chip according to Embodiment 1.

Figure 4:
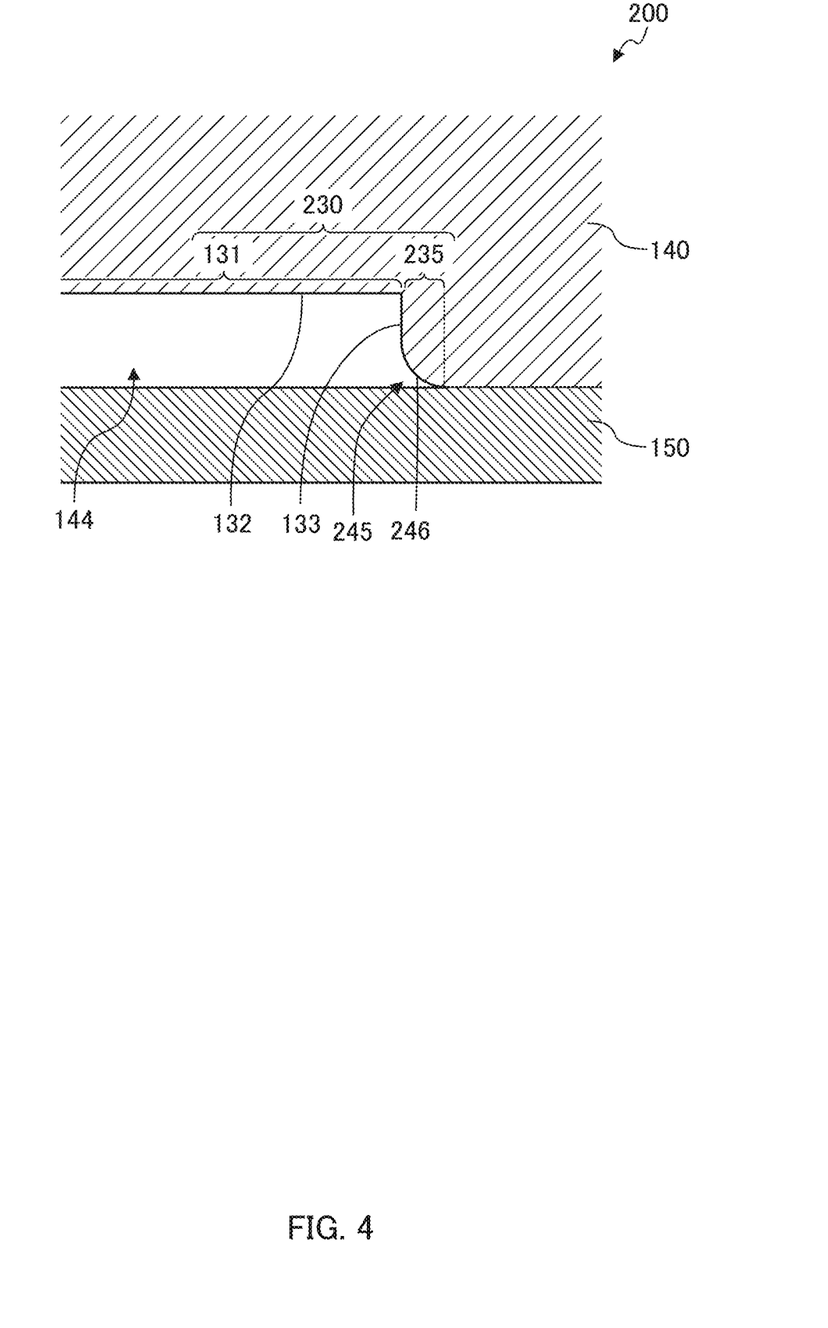
FIG. 4 is a partially enlarged cross-sectional view of a microchannel chip according to a modification example of Embodiment 1.

FIG. 4 is a partially enlarged cross-sectional view showing the configuration of microchannel chip 200 according to the modification example of Embodiment 1 (corresponding to FIG. 2). Microchannel chip 200 is different from microchannel chip 100 in that the cross-sectional (channel cross section) shape of the channel in the direction of movement of the liquid is not rectangular. In the following description, channel 230 of microchannel chip 200 will be described. The same reference numerals will be attached to the same components as in microchannel chip 100 and description thereof will be omitted.

As shown in FIG. 4, channel 230 has first channel 131 and second channel 235. First channel 131 is formed by film 150 closing an opening of first groove 144 which is formed on substrate 140. An open edge of first groove 144 is chamfered on R surface 246. An area that is chamfered on R surface 246 from first groove 144 is second groove 245. Second channel 235 is formed by film 150 closing an opening of second groove 245.

Second channel 235 moves the liquid faster than the speed of movement of the liquid moving through first channel 131. Although not particularly shown, one end part of second channel 235 communicates with first concave part 110, and the other end part communicates with second concave part 120. Second channel 235 is placed in an area on the film 150 side of first lateral surface 133 of first channel 131. In other words, second channel 235 is placed at the depth-direction lower end part of first lateral surface 133. Second channel 235 is configured to have the above-described R surface 246, and an inner surface of film 150 that opposes R surface 246. Second channel 235 has an opening in first channel 131 (first lateral surface 133).

[Effect]

As above, microchannel chips 100 and 200 according to Embodiment 1 have second channels 135 and 235 that are shallower in depth than first channel 131 on the lateral surface of first channel 131. As described above, the liquid moving through first channel 131 is moved to be pulled by the liquid moving through second channels 135 and 235 which are disposed at both of the width-direction ends. In the central part and both of the end parts in the width direction of channel 130, the liquid is moved almost uniformly. Accordingly, in microchannel chips 100 and 200 according to Embodiment 1, bubbles do not remain in channel 230. The liquid moving through channels 130 and 230 moves relatively faster than the channel that does not have second channels 135 and 235.

Further, in microchannel chips 100 and 200 according to Embodiment 1, second channels 135 and 235 are placed in the vicinity of an open edge of first channel 131, and thus the manufacturing is facilitated in the case of integral molding by injection molding.

Embodiment 2

A microchannel chip according to Embodiment 2 of the present invention is different from microchannel chips 100 and 200 of Embodiment 1 in that a first liquid reservoir part is provided between a channel and a first through hole and in that a second liquid reservoir part is provided between the channel and a second through hole. The same reference numerals will be attached to the same components as in microchannel chips 100 and 200 according to Embodiment 1 and description thereof will be omitted.

[Configuration of Microchannel Chip]

Figure 5A:
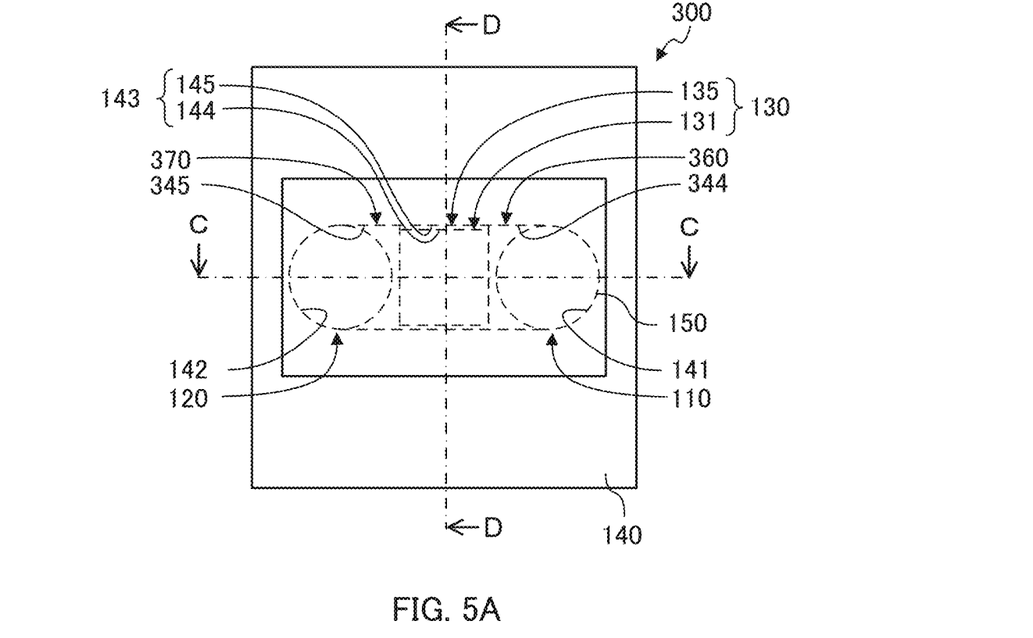
FIGS. 5A to 5C are views showing the configuration of a microchannel chip according to Embodiment 2.
Figure 5B:
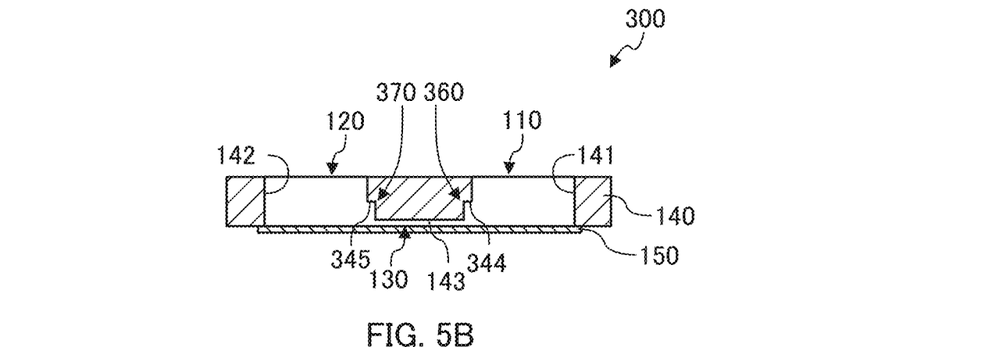
Figure 5C:
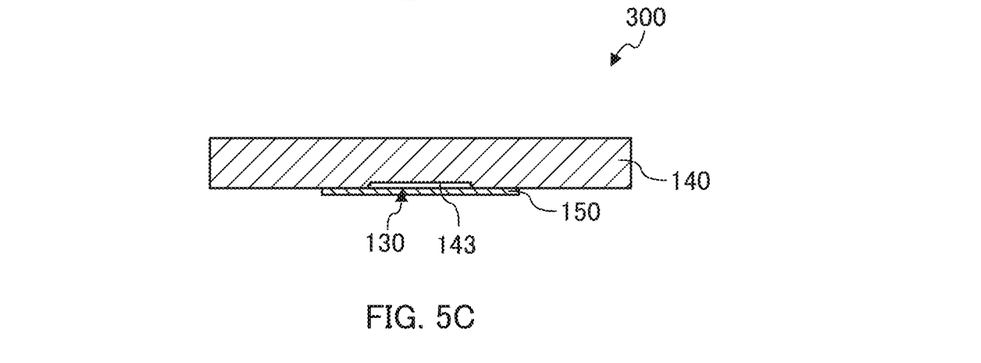

FIGS. 5A to 5C are views showing the configuration of microchannel chip 300 according to Embodiment 2. FIG. 5A is a bottom view of microchannel chip 300, FIG. 5B is a cross-sectional view taken along line C-C shown in FIG. 5A, and FIG. 5C is a cross-sectional view taken along line D-D shown in FIG. 5A.

As shown in FIGS. 5A to 5C, microchannel chip 300 includes substrate 140 and film 150.

Substrate 140 is provided with first liquid reservoir step part 344 and second liquid reservoir step part 345 in addition to first through hole 141, second through hole 142, and groove 143. Since an opening on an opening side of groove 143 is closed by film 150, each of first through hole 141 and second through hole 142 is a bottomed concave part (first concave part 110 and second concave part 120). Since the opening is closed by film 150, groove 143 is channel 130 (refer to FIGS. 5B and 5C for both). Since the opening is closed by film 150, first liquid reservoir stepped portion 344 and second liquid reservoir stepped portion 345 are first liquid reservoir part 360 and second liquid reservoir part 370 (refer to FIG. 5B for both).

First concave part 110 communicates with first liquid reservoir part 360. Second concave part 120 communicates with second liquid reservoir part 370.

First liquid reservoir part 360 temporarily stores a liquid that is introduced from first concave part 110. One end part of first liquid reservoir part 360 communicates with first concave part 110, and the other end part communicates with channel 130. The open shape of the end part on a channel 130 side of first liquid reservoir part 360 is rectangular. In this manner, the liquid that is stored in first liquid reservoir part 360 is moved to channel 130 almost at the same time as the width direction of channel 130.

Second liquid reservoir part 370 temporarily stops the movement of the liquid from channel 130. One end part of second liquid reservoir part 370 communicates with second concave part 120, and the other end part communicates with channel 130. The open shape of the end part on a channel 130 side of second liquid reservoir part 370 is rectangular. The depth of second liquid reservoir part 370 is deeper than channel 130. In this manner, the liquid that reaches second liquid reservoir part 370 from channel 130 in advance is not moved to second liquid reservoir part 370 until channel 130 is filled with a liquid. In this manner, the liquid amount can be adjusted when properties of a liquid are examined by using channel 130 as a chamber.

Film 150 is a transparent and approximately rectangular resin film bonded to one of surfaces of substrate 140 (refer to FIG. 5A). Film 150 covers the opening of groove 143, an opening of first through hole 141 on the opening side of groove 143, an opening of second through hole 142 on the opening side of groove 143, and openings of first liquid reservoir stepped portion 344 and second liquid reservoir stepped portion 345.

Figure 6A:
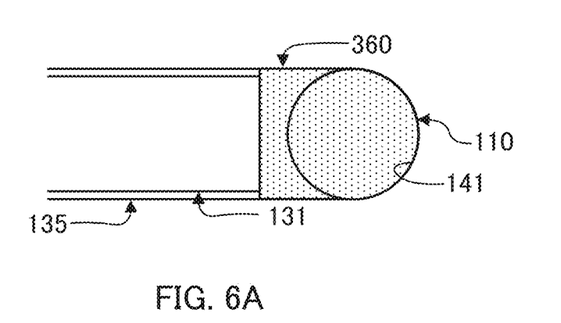
FIGS. 6A to 6C are schematic views showing the movement of a liquid in a channel of the microchannel chip according to Embodiment 2.
Figure 6B:
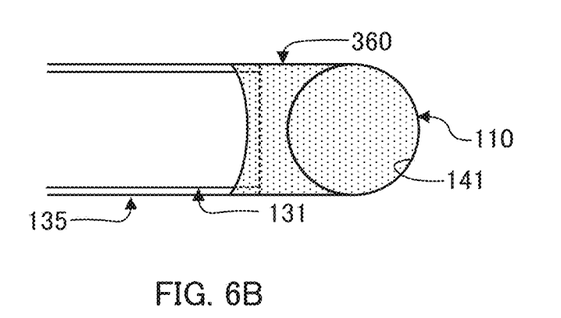
Figure 6C:
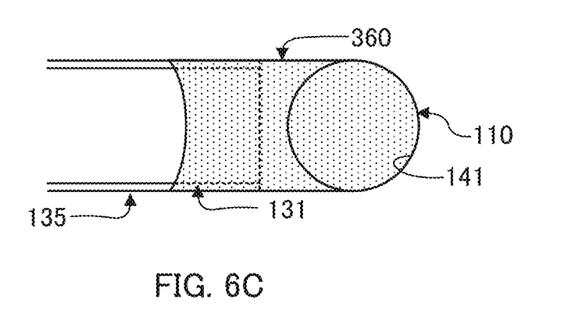

FIGS. 6A to 6C are schematic views (partially enlarged plan views) showing the movement of the liquid in a channel of microchannel chip 300 according to Embodiment 2. As shown in FIG. 6, when the liquid is introduced from first concave part 110 and first liquid reservoir part 360 is filled with the liquid, the movement of the liquid is started on the basis of a capillary phenomenon in first channel 131 and second channel 135 at the same time (refer to FIG. 6A). At this time, the liquid moving through second channel 135 moves faster than the liquid moving through first channel 131. Accordingly, the liquid moving through first channel 131 is moved to be pulled by the liquid moving through second channel 135 which is disposed at both of the width-direction ends (refer to FIGS. 6B and 6C). In this manner, the speed of movement of the liquid is almost uniform in channel 130, and bubbles do not remain in channel 130.

[Effect]

As above, microchannel chip 300 according to Embodiment 2 has the same effect as microchannel chips 100 and 200 according to Embodiment 1.

Embodiment 3

A microchannel chip according to Embodiment 3 of the present invention is different from microchannel chips 100, 200, and 300 according to Embodiments 1 and 2 in that a liquid is configured to be operated from a lateral surface where film 450 of substrate 440 is placed. Hereinafter, the microchannel chip according to Embodiment 3 of the present invention will be described.

[Configuration of Micro Channel Chip]

Figure 7A:
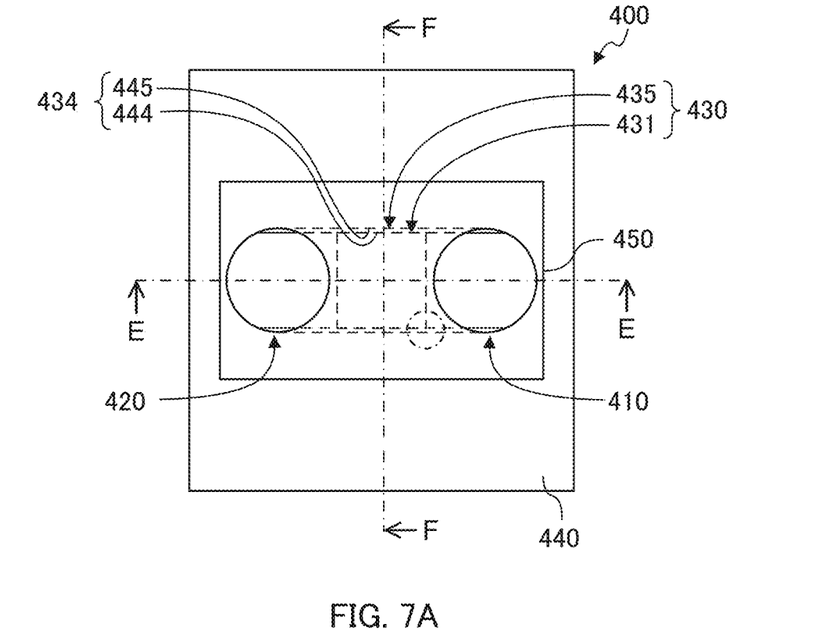
FIGS. 7A to 7C are views showing the configuration of a microchannel chip according to Embodiment 3.
Figure 7B:
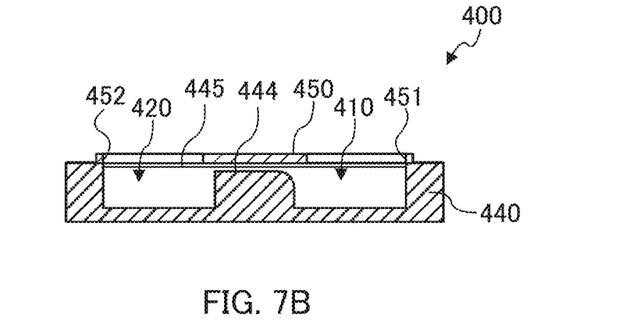
Figure 7C:
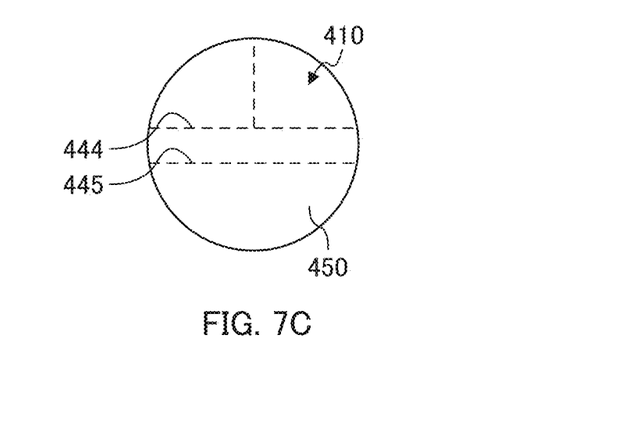
Figure 8A:
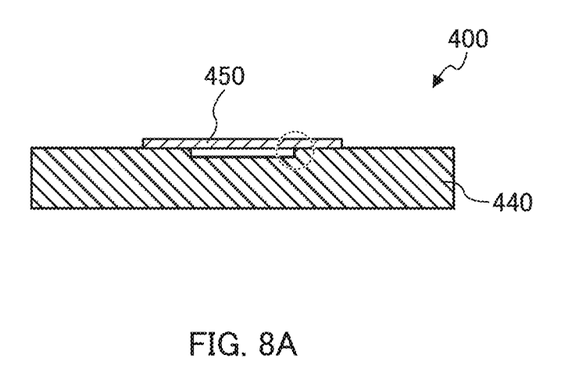
FIGS. 8A and 8B are views showing the configuration of the microchannel chip according to Embodiment 3.
Figure 8B:
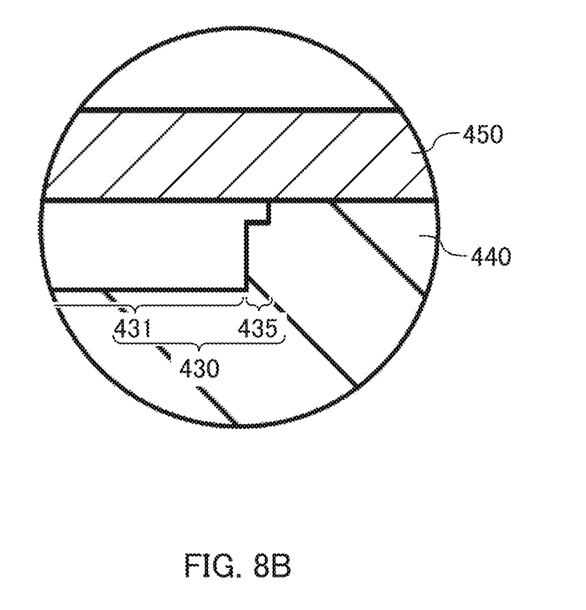
Figure 9A:
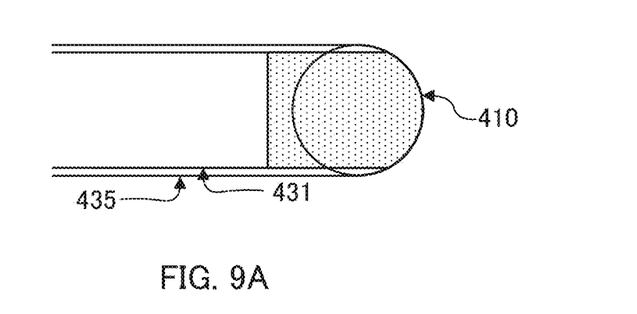
FIGS. 9A to 9D are schematic views showing the movement of a liquid in a channel of the microchannel chip according to Embodiment 3.
Figure 9B:
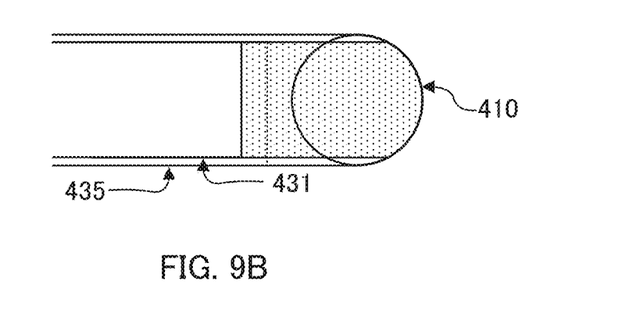
Figure 9C:
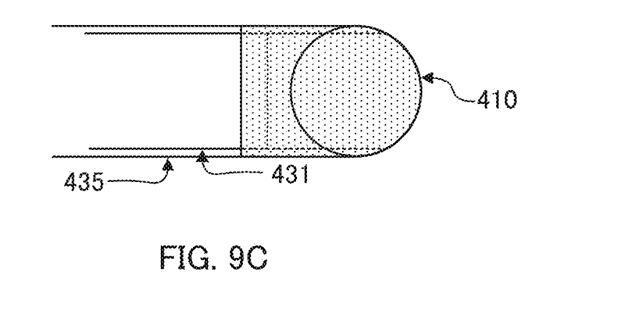
Figure 9D:
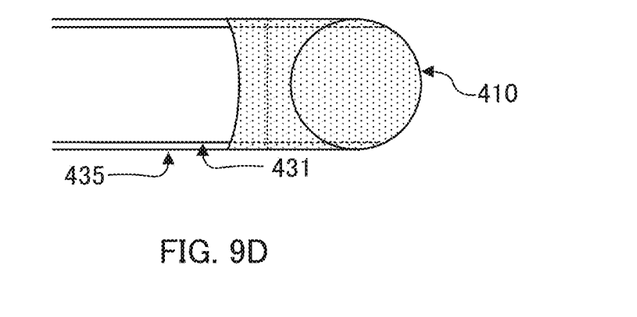

FIGS. 7A to 8B are views showing the configuration of microchannel chip 400 according to Embodiment 3. FIG. 7A is a plan view of microchannel chip 400, FIG. 7B is a cross-sectional view taken along line E-E shown in FIG. 7A, and FIG. 7C is a partially enlarged cross-sectional view showing the area surrounded by the broken line shown in FIG. 7A. FIG. 8A is a cross-sectional view taken along line F-F shown in FIG. 7A, and FIG. 8B is a partially enlarged cross-sectional view showing the area surrounded by the broken line shown in FIG. 8A.

As shown in FIGS. 7A to 8B, microchannel chip 400 includes substrate 440 and film 450.

Substrate 440 has first concave part 410, second concave part 420, and groove 434. First concave part 410 and second concave part 420 open on a surface where groove 434 of substrate 440 is formed. Since the opening is closed by film 450, groove 434 is channel 430.

First concave part 410 is a bottomed concave part, and communicates with one end part of channel 430. Second concave part 420 is a bottomed concave part, and communicates with the other end part of channel 430. The plan view shape of first concave part 410 and second concave part 420 is not particularly limited, and examples thereof include a bell shape. An area on a groove 434 side of first concave part 410 and an area on a groove 434 side of second concave part 420 are covered by film 450. The depth of first concave part 410 and second concave part 420 is not particularly limited. The depth of first concave part 410 and second concave part 420 can be appropriately adjusted according to the amount of a liquid in use.

Groove 434 has first groove 444 and second groove 445. First groove 444 and second groove 445 have openings closed by film 450, and are first channel 431 and second channel 435, respectively. A communication section between first groove 434 and first concave part 410 is R-chamfer processed. The liquid can be introduced from first concave part 410 across the entire width direction of first channel 431 almost at the same time by R-chamfer processing an end part of first groove 444. If the end part of first groove 444 is R-chamfer processed, the speed of the liquid can be further uniform in a central part and both end parts in the width direction of first channel 431 than in a case where the end part of first groove 444 is not R-chamfer processed. The radius of curvature of the communication section (an R surface) in a cross section of the direction of movement of the liquid is not particularly limited. It is preferable that the radius of curvature of the communication section (the R surface) be at least 0.4 mm. In a case where the radius of the communication section is smaller than 0.4 mm, there is a concern that the above-described effect could not be sufficiently achieved. In a case where any treatment is performed between first concave part 410 and second concave part 420 (for example, in a case where a sample in the liquid is captured on a bottom surface of first channel 431 or the captured sample is irradiated with light), the radius of curvature of the communication section (the R surface) is set not to be so excessively high as to have a negative impact on the treatment. Accordingly, the communication section may be R-chamfer processed by the extent to which the effect of making the speed of the liquid in the width direction of first channel 431 further uniform is achieved.

One end part of first channel 431 communicates with first concave part 410, and the other end part communicates with second concave part 420. One end part of second channel 435 communicates with first concave part 410, and the other end part communicates with second concave part 420. Second channel 435 is placed in an area on a film 450 side of first channel 431. In other words, second channel 435 is placed at a depth-direction upper end part of first lateral surface 133. The cross-sectional shape of second channel 435 is not particularly limited. In examples shown in FIGS. 7A to 8B, the cross-sectional shape of second channel 435 is rectangular.

Film 450 has third through hole 451 and fourth through hole 452. Film 450 covers an opening of groove 434, a part of an opening of first concave part 410 (a part of the groove 434 side), and a part of an opening of second concave part 420 (a part of the groove 434 side). The shape of third through hole 451 and fourth through hole 452 is not particularly limited, and examples thereof include a circular shape. The diameter of third through hole 451 and fourth through hole 452 is the same as the width-direction length of groove 434.

FIGS. 9A to 9D are schematic views (partially enlarged plan views) showing the movement of the liquid in the channel of microchannel chip 400 according to Embodiment 3. When the liquid is introduced to first concave part 410, first concave part 410 is filled with the liquid from a bottom surface (refer to FIG. 9A). When the liquid is introduced to first concave part 410, the liquid reaches an inlet of first channel 431 (refer to FIG. 9B) in a state where first channel 431 is widened in the width direction by an R surface effect and the liquid also reaches second channel 435 (refer to FIG. 9C). Then, the movement of the liquid is started on the basis of a capillary phenomenon in first channel 431 and second channel 435 (refer to FIG. 9D). At this time, the movement of the liquid moving through second channel 435 is sufficiently faster than the movement of the liquid moving through first channel 431. Therefore, the liquid moving through first channel 431 is moved to be pulled by the liquid moving through second channel 435 which is disposed at both width-direction ends. In this manner, the speed of movement of the liquid is almost uniform in channel 430, and bubbles do not remain in channel 430.

Modification Example

Microchannel chips 500 and 600 according to a modification example of Embodiment 3 are different from microchannel chip 400 in that the cross-sectional shape of second channels 535 and 635 in a direction which is orthogonal to the direction of movement of a liquid is rectangular. In the following description, the same reference numerals will be attached to the same components as in microchannel chip 400 and description thereof will be omitted. Hereinafter, only channels 530 and 630 of microchannel chip 500 will be described.

Figure 10A:
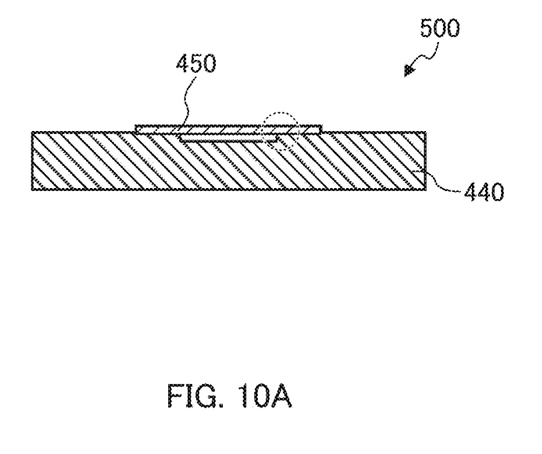
FIGS. 10A to 10D are views showing the configuration of a microchannel chip according to a modification example of Embodiment 3.
Figure 10B:
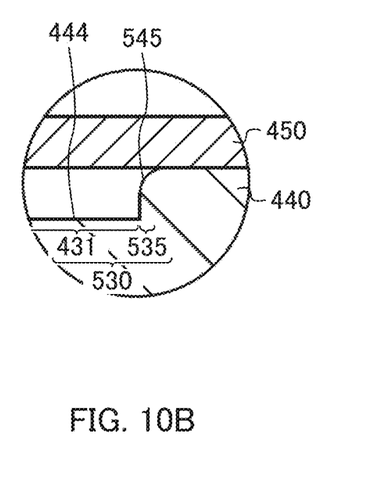
Figure 10C:
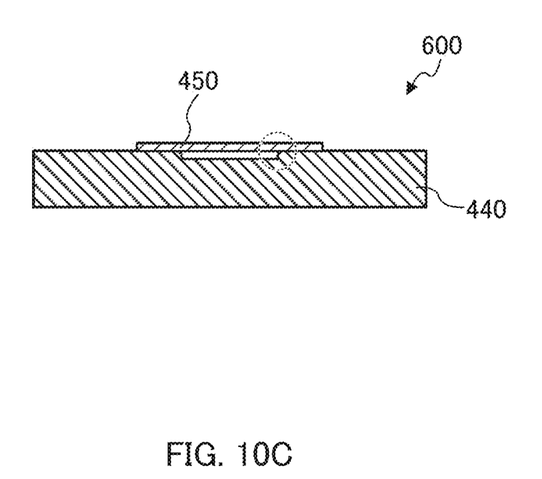
Figure 10D:
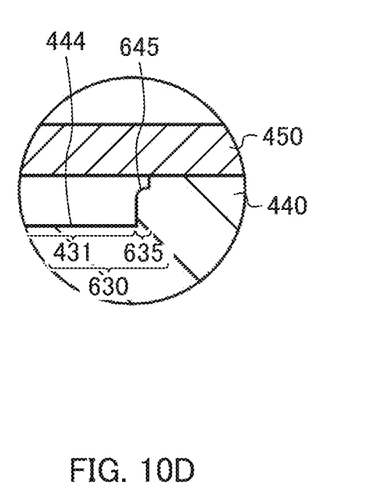

FIGS. 10A to 10D are partially enlarged cross-sectional views showing the configuration of microchannel chip 500 according to the modification example of Embodiment 3 (corresponding to FIG. 8). FIG. 10A is a cross-sectional view of microchannel chip 500 according to the modification example of Embodiment 3 (corresponding to FIG. 8A), FIG. 10B is a partially enlarged cross-sectional view showing the area shown by the broken line of FIG. 10A (corresponding to FIG. 8B), FIG. 10C is a cross-sectional view of microchannel chip 500 according to another modification example of Embodiment 3 (corresponding to FIG. 8A), and FIG. 10D is a partially enlarged cross-sectional view showing the area shown by the broken line of FIG. 10C (corresponding to FIG. 8B).

As shown in FIGS. 10A and 10B, channel 530 has first channel 431 and second channel 535. First channel 431 is formed by film 450 closing an opening of first groove 444 that is formed on substrate 440. An open edge of first groove 444 is chamfered on the R surface. An area that is chamfered on the R surface from first groove 444 is second groove 545. Second channel 535 is formed by film 450 closing an opening of second groove 545.

As shown in FIGS. 10C and 10D, channel 630 has first channel 431 and second channel 635. Second groove 645 has a portion whose cross-sectional shape is rectangular and a portion where an interface between the portion whose cross-sectional shape is rectangular and first groove 444 is chamfered on the R surface. Second channel 635 is formed by film 450 closing an opening of second groove 645.

[Effect]

As above, microchannel chips 400, 500, and 600 according to Embodiment 3 can make the flow of the liquid further uniform in the width direction of channels 430, 530, and 630 than microchannel chips 100, 200, and 300 according to Embodiments 1 and 2 can. Therefore, in microchannel chips 400, 500, and 600 according to Embodiment 3, bubbles do not remain in channels 430, 530, and 630.

In microchannel chips 400, 500, and 600 according to Embodiment 3, both of the communication section between first groove 444 and second concave part 420 and the communication section between second groove 445 and second concave part 420 are not R-chamfer processed. Accordingly, the movement of the liquid to second concave part 420 can be suppressed until channel 430 is filled with the liquid as is the case with second liquid reservoir part 370 of microchannel chip 300 according to Embodiment 2.

INDUSTRIAL APPLICABILITY

The liquid handling apparatus according to the present invention is useful as a microchannel chip that is used in the fields of science, medicine, and the like.

REFERENCE SIGNS LIST 100, 200, 300, 400, 500, 600 Microchannel chip
110, 410 First concave part
120, 420 Second concave part
130, 230, 430, 530, 630 Channel
131, 431 First channel
132 First bottom surface
133 First lateral surface
135, 235, 435, 535, 635 Second channel
136 Second bottom surface
137 Second lateral surface
140, 440 Substrate
141 First through hole
142 Second through hole
143, 434 Groove
144, 444 First groove
145, 245, 445, 545, 645 Second groove
150, 450 Film
451 Third through hole
452 Fourth through hole
246 R surface
344 First liquid reservoir stepped portion
345 Second liquid reservoir stepped portion
360 First liquid reservoir part
370 Second liquid reservoir part

The invention claimed is:
1. A liquid handling apparatus comprising:
a substrate that includes a groove which is a channel through which a liquid can be moved on the basis of a capillary phenomenon by an opening of the groove being closed; and
a film that is bonded to the substrate to cover the opening of the groove, wherein the channel has a main channel and a guide channel disposed along the main channel,
wherein the main channel comprises a first bottom surface, a pair of first lateral surfaces that are placed at both width-direction end parts of the first bottom surface, and an inner surface of the film that opposes the first bottom surface,
wherein the guide channel comprises a second bottom surface, a second lateral surface placed at one width- direction end part of the second bottom surface and the inner surface of the film that opposes the second bottom surface, wherein the guide channel is formed in a groove shape that has an opening in the main channel along the first lateral surface, wherein the groove has a main groove that is the main channel by the film being bonded to the substrate, and a guide groove that is the guide channel by the film being bonded to the substrate, opens on the first lateral surface of the main groove, and has a width narrower than the width of the main groove, and wherein the guide groove is placed in an area on a film side of the first lateral surface of the main groove and is shallower than the main groove.

2. The liquid handling apparatus according to claim 1, wherein the cross-sectional shape in a direction orthogonal to the direction of movement of the liquid in the guide channel is rectangular.

3. The liquid handling apparatus according to claim 1, wherein an open edge of the main groove is chamfered on an R surface, and
wherein the guide channel is formed by the R surface and the film.

4. The liquid handling apparatus according to claim 1, wherein the substrate further includes a first through hole that communicates with one end part of the groove, and a second through hole that communicates with the other end part of the groove, and
wherein the film is bonded to the substrate to cover the opening of the groove, an opening of the first through hole on an opening side of the groove, and an opening of the second through hole on the opening side of the groove.

5. The liquid handling apparatus according to claim 4, wherein the substrate further includes a first liquid reservoir stepped portion that is placed between the groove and the first through hole, and a second liquid reservoir stepped portion that is placed between the groove and the second through hole, and
wherein the film is bonded to the substrate to further cover openings of the first liquid reservoir stepped portion and the second liquid reservoir stepped portion.

6. The liquid handling apparatus according to claim 1, wherein the film and the substrate are bonded to each other by thermocompression,
wherein the guide groove has a depth of at least 20 pm and is shallower than the main groove, and
wherein inner surfaces of the main channel and the guide channel are lyophilic.

7. The liquid handling apparatus according to claim 1, wherein the substrate further includes a bottomed first concave part that opens on a surface where the groove is formed and communicates with one end part of the groove, and a bottomed second concave part that opens on the surface where the groove is formed and communicates with the other end part of the groove,
wherein the first concave part and the second concave part are open via a through hole that is formed on the film, and
wherein a communication section between the main groove and the first concave part is chamfered on an R surface.

* * * * *